United States Patent
Klapötke et al.

(10) Patent No.: US 9,481,656 B2
(45) Date of Patent: Nov. 1, 2016

(54) 3,3'-DINITRO-5,5'-BIS-TRIAZOLE-1,1'-DIOL

(71) Applicant: LUDWIG MAXIMILIANS-UNIVERSITÄT MÜNCHEN, München (DE)

(72) Inventors: Thomas M. Klapötke, München (DE); Alexander Dippold, München (DE)

(73) Assignee: Ludwig-Maximilians-Universität München, München (DE)

( * ) Notice: Subject to any disclaimer, the term of this patent is extended or adjusted under 35 U.S.C. 154(b) by 17 days.

(21) Appl. No.: 14/649,146

(22) PCT Filed: Nov. 22, 2013

(86) PCT No.: PCT/EP2013/074500
§ 371 (c)(1),
(2) Date: Jun. 2, 2015

(87) PCT Pub. No.: WO2014/086599
PCT Pub. Date: Jun. 12, 2014

(65) Prior Publication Data
US 2016/0024029 A1    Jan. 28, 2016

(30) Foreign Application Priority Data

Dec. 3, 2012  (DE) .......... 10 2012 222 086
Dec. 6, 2012  (DE) .......... 10 2012 222 424

(51) Int. Cl.
C07D 249/14    (2006.01)
C06B 25/34     (2006.01)
C06B 25/00     (2006.01)

(52) U.S. Cl.
CPC ............ *C07D 249/14* (2013.01); *C06B 25/00* (2013.01); *C06B 25/34* (2013.01)

(58) Field of Classification Search
CPC .................................. C07D 249/14
See application file for complete search history.

(56) References Cited

FOREIGN PATENT DOCUMENTS

WO    WO 2005/035466 A2    4/2005

OTHER PUBLICATIONS

Database Registry (Online) Chemical Abstracts Service, Columbus, Ohio, US; Jan. 11, 2012, Chemical Library: XP002723640, Database accession No. 382159-83-3.
Tselinkskii, I. V., et al.: "Synthesis and study of thermal stability of 3-nitro-1, 2, 4-triazole N-azidomethyl derivatives," Russian Chemical Bulletin, International Edition, vol. 58, No. 11, pp. 2356-2361, Nov. 2009.
Dippold, Alexander A., et al.: "A Study of Dinitro-bis-1, 2, 4-triazole-1, 1'-diol and Derivatives: Design of High-Performance Insensitive Energetic Materials by the Introduction of N-Oxides," Journal of the American Chemical Society., vol. 135, 2013, pp. 9931-9937.
International Preliminary Report on Patentability issued in PCT/EP2013/074500, 5 pages, mailed Jun. 9, 2015.

*Primary Examiner* — Michael Barker
*Assistant Examiner* — Karen Cheng
(74) *Attorney, Agent, or Firm* — Kagan Binder, PLLC

(57) ABSTRACT

The invention relates to 3,3'-dinitro-5,5'-bis-triazole-1,1'-diol and to salts thereof, and to an energetic active mass comprising said salts.

12 Claims, 2 Drawing Sheets

3,3'-DINITRO-5,5'-BIS-TRIAZOLE-1,1'-DIOL

This application claims benefit from International Application No. PCT/EP2013/074500, which was filed on Nov. 22, 2013, which in turn claims priority to E.P. Patent Application 10 2012 222 424.6 filed on Dec. 6, 2012 which in turn claims priority to E.P. Patent Application 10 2012 222 086.0 filed on Dec. 3, 2012 wherein these patent applications are incorporated herein by reference in their entireties.

It is known to use nitroamines, such as hexogen (RDX), octogen (HMX), or hexanitrohexaazaisowurtzitane (CL-20) as secondary explosives. A drawback of these nitroamines and their reaction products following a detonation resides in their toxicity and in the ecological damage caused thereby. There is, however, a need for higher-performance secondary explosives. These are in fact already known, for example in the form of dinitroazofuroxan or octanitrocubane. However, a disadvantage of these substances resides in the fact that for secondary explosives they are highly sensitive and the synthesis thereof is very elaborate and involves ten or more reaction steps. Furthermore, there is a need for thermally highly stable explosives having better energetic performance and a higher thermal stability than that of the hexanitrostilbene (HNS) usually employed.

It is an object of the present invention to provide an alternative energetic active mass which is easy to synthesize and exhibits high efficiency together with safe handling and high thermal stability and also causes an acceptable degree of ecological damage. A further object is to indicate possible ingredients of said energetic active mass and to indicate a starting material for the production of said ingredients. In addition, a use of one of the ingredients, a method for the production of the starting material and also a method for the production of one of the ingredients of the energetic active mass shall be indicated.

The above objects are achieved by the features of claims 1, 2, 4, 5, 6, and 10. Suitable embodiments are indicated by the features of claims 3 and 7 to 9.

According to the invention, 3,3'-dinitro-5,5'-bis-triazole-1,1'-diol and a salt thereof, more particularly a dihydroxylammonium salt, a diguanidinium salt or a di-triaminoguanidinium salt thereof, are provided. Furthermore, an energetic active mass comprising a dihydroxylammonium salt, a diguanidinium salt or a di-triaminoguanidinium salt of 3,3'-dinitro-5,5'-bis-triazole-1,1'-diol is provided. By an energetic active mass is meant in this case an active mass which on ignition reacts in a deflagrative manner or by detonation. It may be a pyrotechnic active mass. The dihydroxylammonium salt of 3,3'-dinitro-5,5'-bis-triazole-1,1'-diol (MAD-X1) shows a detonation velocity in the range of the detonation velocity of CL-20, which is higher than that of RDX by approximately 500 $ms^{-1}$. MAD-X1 thus satisfies the prerequisites required for a high-performance explosive. Calculation of the detonation velocities was carried out using the program EXPLO5, Version 5.05 (M. Sućeska, EXPLO5.04 program, Zagreb, Croatia, 2011; M. Sućeska, Calculation of detonation parameters by EXPLO5 computer program, *Materials Science Forum*, 2004, 465-466, 325-330; M. Sućeska, Calculation of the detonation properties of C—H—N—O explosives, *Propellants, Explos., Pyrotech.* 1991, 16, 197-202; M. Sućeska, Evaluation of detonation energy from EXPLO5 computer code results, *Propellants, Explos., Pyrotech.* 1999, 24, 280-285; M. L. Hobbs, M. R. Baer, *Proc. of the $10^{th}$ Symp. (International) on Detonation*, ONR 33395-12, Boston, Mass., Jul. 12-16, 1993, p. 409).

In addition, the sensitivity of MAD-X1 is excellent. While RDX, when tested for impact sensitivity by the drop hammer method, already reacts at 7.5 J and must be desensitized for use by the addition of binding agents and plasticizers, MAD-X1 is already completely insensitive with regard to impact and friction. Using the drop hammer method, a reaction was only observed above 40 J, and the sensitivity to friction as measured by a friction apparatus required 360 N to cause a reaction. On account of the insensitivity in relation to external stimuli, the degree of safety provided during manufacture and handling is significantly higher than that provided by other energetic active masses. MAD-X1 is therefore very suitable for the production of insensitive munition. Moreover, the density of MAD-X1 is distinctly higher than that of RDX. Furthermore, an active mass containing MAD-X1 requires no additives for desensitization and also, on account of the low density of these additives, exhibits a distinctly higher density than an active mass containing RDX. This means that for a given volume a greater weight of an active mass containing MAD-X1 can be accommodated and thus a higher performance than with RDX can be achieved.

The diguanidinium salt of 3,3'-dinitro-5,5'-bis-triazole-1,1'-diol (MAD-X2) does not satisfy the prerequisites required for a high-performance explosive but instead has excellent properties with regard to thermal stability and insensitivity to external stimuli. It decomposes at a heat-up rate of 5° C./min only at a temperature of 341° C. and thus exceeds by far the decomposition temperature of RDX and even the decomposition temperature of HNS. In addition, the detonation velocity of 8242 $cm^{-1}$ is higher than that of the commonly used heat-resistant explosive HNS.

The triaminoguanidinium salt of 3,3'-dinitro-5,5'-bis-triazole-1,1'-diol (MAD-X3) combines a high detonation velocity, which is in the range of the detonation velocity of RDX, with a very high nitrogen content of 60.07%. On burn-up or during detonation, the high nitrogen content causes the formation of a relatively large volume of gas. In combination with the high detonation velocity it is in this way possible to provide a very strong impulse. Thus MAD-X3 is particularly suitable for use as a propellant. Furthermore, a high nitrogen to $CO_2$ ratio reduces corrosion at launching tubes containing iron, when MAD-X3 is used as propellant for a projectile, since by this means the formation of iron carbide is reduced. In addition, MAD-X3 shows moderate sensitivity to friction (360 N) and impact (10 J). MAD-X1, MAD-X2, and MAD-X3 can in each case be used as an explosive, as a propellant, as a pyrotechnic gas-producing means, for example in a gas generator, or as an additive to a solid propellant.

The properties of MAD-X1, MAD-X2, and MAD-X3 compared with pentaerythritol tetranitrate (PETN), RDX, β-HMX, ε-CL-20 and HNS are given in the following table:

|  | PETN | RDX | β-HMX | ε-CL20 | HNS | MAD-X1 | MAD-X2 | MAD-X3 |
| --- | --- | --- | --- | --- | --- | --- | --- | --- |
| Formula | $C_5H_8N_4O_{12}$ | $C_3H_6N_6O_6$ | $C_4H_8N_8O_8$ | $C_6H_6N_{12}O_{12}$ | $C_{14}H_6N_6O_{12}$ | $C_4H_8N_{10}O_8$ | $C_6H_{12}N_{14}O_6$ | $C_6H_{18}N_{20}O_6$ |
| Molecular weight | 316.1 | 222.1 | 296.2 | 438.2 | 450.1 | 324.2 | 376.3 | 466.3 |
| IS [J][a] | 4 | 7.5 | 7 | 4 | 5 | >40 | >40 | 10 |
| FS [N][b] | 80 | 120 | 112 | 48 | 240 | 360 | 360 | 360 |

-continued

| | PETN | RDX | β-HMX | ε-CL20 | HNS | MAD-X1 | MAD-X2 | MAD-X3 |
|---|---|---|---|---|---|---|---|---|
| ESD-Test [J]$^c$ | 0.1 | 0.2 | 0.2 | — | — | 0.5 | 0.8 | 0.2 |
| N [%]$^d$ | 17.72 | 37.8 | 37.8 | 38.3 | 18.7 | 43.21 | 52.12 | 60.07 |
| Ω [%]$^e$ | −10.12 | −21.6 | −21.6 | −11.0 | −67.6 | −19.7 | −51.0 | −51.5 |
| $T_{dec.}$ [° C.]$^f$ | 150 | 210 | 285 | 195 | 320 | 222 | 341 | 220 |
| Density [g cm$^{-3}$]$^g$ | 1.778 | 1.820 | 1.905 | 2.038 | 1.74 | 1.952 | 1.788 | 1.75 |
| $\Delta_f U$ °/kJ kg$^{-1}$ $^h$ | −1611 | 417 | 353 | 982 | 240 | 756 | 366 | 1858 |
| $-\Delta_E U$ ° [kJ kg$^{-1}$]$^i$ | 6190 | 6125 | 6063 | 6473 | 5474 | 5980 | 4163 | 5105 |
| $T_E$ [K]$^j$ | 4306 | 4236 | 4117 | 4654 | 3982 | 4132 | 3038 | 3393 |
| $p_{C-J}$ [kbar]$^k$ | 320 | 348 | 392 | 446 | 242 | 413 | 276 | 316 |
| D [m s$^{-1}$]$^l$ | 8320 | 8748 | 9058 | 9342 | 7446 | 9253 | 8242 | 8802 |
| Gas volume [l kg$^{-1}$]$^m$ | 688 | 739 | 734 | 669 | 530 | 740 | 770 | 817 |

$^a$Impact sensibility (measured by the drop hammer method according to the German Federal Institute for Materials Research and Testing);
$^b$friction sensibility (measured using a friction apparatus according to the German Federal Institute for Materials Research and Testing);
$^c$measured by means of the electrostatic discharger sold by OZM Research s.r.o., Czech Republic;
$^d$nitrogen content;
$^e$oxygen balance;
$^f$decomposition temperature according to DSC (Differential Scanning Calorimetry) measurement (5° C. per minute);
$^g$determined by X-ray diffraction at approximately 100K;
$^h$ energy of formation calculated by the CBS-4M method;
$^i$explosive energy;
$^j$explosion temperature;
$^k$detonation pressure;
$^l$detonation velocity;
$^m$determined on the assumption of exclusively gaseous reaction products.

Another advantage resides in the synthesis of MAD-X1, MAD-X2, and MAD-X3, that can take place in a simple manner using low-cost starting materials and involving only a small number of synthesis steps. The final synthesis step can in all cases take place in ethanol, from which the ethanol-insoluble compounds MAD-X1, MAD-X2, and MAD-X3 precipitate as an amorphous powder. This is advantageous for the formulation of an energetic active mass, since, owing to the low surface to volume ratio of the spherical particles of the powder, compared with needles frequently formed in the case of other explosive syntheses, less or no plasticizer and less binding agent are required for the production of the active mass. This makes for a higher content of explosive in the active mass and thus a greater performance of the active mass. Furthermore, the compounds MAD-X1, MAD-X2, and MAD-X3 are poorly soluble in water. This is advantageous for further processing of the salts.

In a performance test using the so-called SSSRT (Small Scale Shock Reactivity Test), which examines the degree of bulge caused in an aluminum block by a test explosive on detonation thereof, it was found that MAD-X1, following ignition thereof, had a similar performance to β-HMX and a higher performance than RDX.

Since it is known that with the SSSRT less sensitive explosives must be used in larger quantities in order to demonstrate their performance and more sensitive explosives having a lower performance reveal an apparently higher performance, it may be assumed that the actual performance of MAD-X1 exceed the performance of β-HMX.

The invention further relates to the use of a dihydroxylammonium salt, diguanidinium salt, or di-triaminoguanidinium salt of 3,3'-dinitro-5,5'-bis-triazole-1,1'-diol as an explosive, a propellant, a pyrotechnic gas-producing means, or as an additive to a solid propellant, and also to a method for the production of 3,3'-dinitro-5,5'-bis-triazole-1,1'-diol, in which 3,3'-dinitro-5,5'-bis-(1H-1,2,4-triazole) (DNBT) is oxidized to the 3,3'-dinitro-5,5'-bis-(1,2,4-triazole)-1,1'-diol (DNBTO).

The DNBT can be oxidized by means of 2KHSO$_5$.KHSO$_4$.K$_2$SO$_4$ or some other inorganic or organic peroxoacid, perborate, hydrogen peroxide, or hypofluorous acid or some other oxygen transfer agent. The oxidation can take place in aqueous solution. 2KHSO$_5$.KHSO$_4$.K$_2$SO$_4$ is marketed by the company DuPont under the trade name of Oxone®. The addition of Oxone® or the other inorganic or organic peroxoacid, perborate, hydrogen peroxide or hypofluorous acid, or the other oxygen transfer agent preferably takes place in excess, in order to assure complete oxidation. Oxidation with Oxone® is superior to other methods with regard to cost and handling. In the event of the oxidation of DNBT, the ratio of Oxone® to DNBT and/or the contact time can be varied. The DNBT can be obtained by diazotization of 3,3'-diamino-5,5'-bis-(1H-1,2,4-triazole) (DABT) in sulfuric acid in the presence of nitrite.

The DABT can be obtained by the reaction of oxalic acid and aminoguanidine bicarbonate in an acid, more particularly in concentrated hydrochloric acid, separation of the intermediate thus formed, and heating of the intermediate in a basic medium.

The invention furthermore relates to a method for the production of dihydroxylammonium salt, diguanidinium salt, or di-triaminoguanidinium salt of 3,3'-dinitro-5,5'-bistriazole-1,1'-diol comprising the following steps:
 a) incubation of DNBTO with hydroxylamine, hydroxylammonium ions, guanidinium carbonate, guanidinium ions, guanidine, or triaminoguanidine in alcoholic solution and
 b) separation of the precipitate thus formed.

The synthesis of MAD-X1, MAD-X2, and MAD-X3 is illustrated diagrammatically below with reference to exemplary embodiments, in which.

Figure 1:
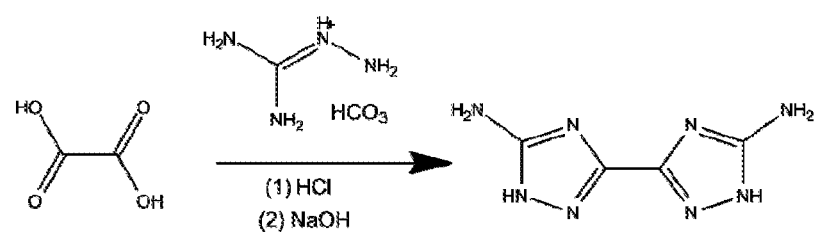
FIG. 1 is a diagrammatic representation of the synthesis of DABT.

1. SYNTHESIS OF DABT 100 mL of concentrated hydrochloric acid were added with stirring to an aqueous solution of 20 g (159 mmol) of oxalic acid and 45.4 g (332 mmol) of aminoguanidine bicarbonate. The solution was stirred for one hour at 70° C. and then allowed to cool down to room temperature. The precipitate thus formed was separated by filtration as a white solid. The separated solid was dissolved in 240 mL of water and adjusted to a pH-value of 14 with sodium hydroxide. The mixture was then refluxed for one hour, and subsequently cooled down to room temperature and acidified to a pH-value of 4 with concentrated acetic acid. A precipitate thus formed was separated by filtration. There were thus obtained 18.6 g (112 mmol) of DABT as colorless solid. This corresponds to a yield of 70%. The synthesis is diagrammatically illustrated in FIG. 1.

2. SYNTHESIS OF DNBT

Figure 2:
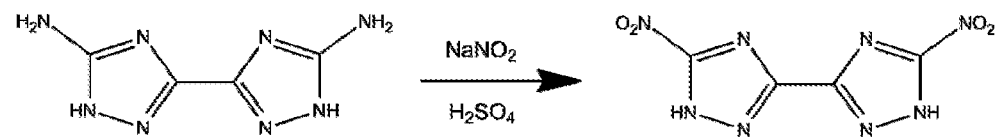
FIG. 2 is a diagrammatic representation of the synthesis of DNBT.

A suspension of 11.9 g (72 mmol) of DABT in 140 mL of 20% sulfuric acid was added dropwise to a solution of 98.8 g (1.4 mol) of sodium nitrite (corresponding to 20 eq.) in 140 mL of water at 50° C. The mixture was subsequently stirred for one hour at 50° C. The reaction mixture was then acidified with 20% sulfuric acid until no further generation of nitrogen dioxide could be observed. The solution was then cooled down to 0° C. The precipitate thus formed was separated by filtration, dissolved in boiling water, and hot filtered to separate insoluble impurities, and the resultant clear solution was left to stand at 5° C. overnight. There was thus formed a pale green precipitate of DNBT-dihydrate as crystalline solid. The solid was separated. The yield was 15.5 g, corresponding to 59 mmol or 82%. The corresponding diazotization reaction is illustrated in FIG. 2.

Figure 3:
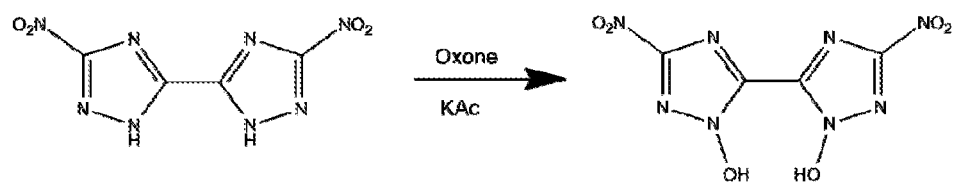
FIG. 3 is a diagrammatic representation of the synthesis of DNBTO.

3. SYNTHESIS OF DNBTO 5 g (19 mmol) of DNBT×2H$_2$O were dissolved in 300 mL of an aqueous solution buffered with 74.7 g (760 mmol) of potassium acetate. To this, 117 g (0.38 mol) of Oxone® were added in portions. The mixture was then stirred for 60 hours at 40° C. Subsequently, the solution was acidified by means of 150 mL of sulfuric acid (50 w/w %) and extracted with 4×100 mL of ethyl acetate. The combined organic phases were dried over magnesium sulfate. The solvent was then evaporated in vacuo. The residue was suspended in 50 mL of benzene and evaporated to complete dryness. Thus there remained 4 g (16 mmol) DNBTO as colorless solid. This corresponds to a yield of 81%. The reaction is illustrated diagrammatically in FIG. 3.

4. SYNTHESIS OF MAD-X1

Figure 4:
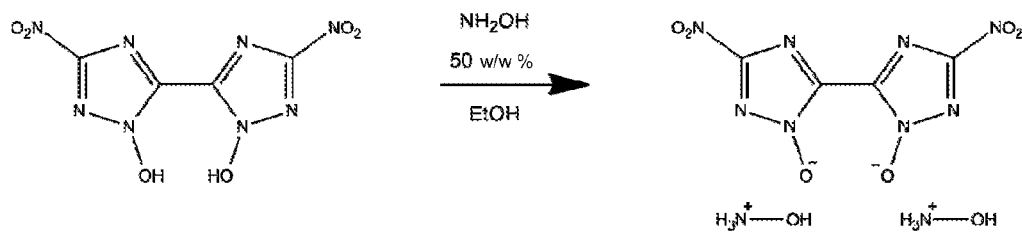
FIG. 4 is a diagrammatic representation of the synthesis of MAD-X1.

0.5 g (1.9 mmol) of DNBTO was dissolved in 50 mL of ethanol. To the solution there was added 0.2 mL of a solution of hydroxylamine in water (50 w/w %, corresponding to 2.2 eq.). The mixture was stirred for 10 min and the precipitate formed was separated by filtration as an orange-colored solid. The separated solid was dried in air. There was thus obtained 0.6 g (1.9 mmol) of MAD-X1. This corresponds to a yield of 95%. The reaction is diagrammatically illustrated in FIG. 4.

5. SYNTHESIS OF MAD-X2

Figure 5:
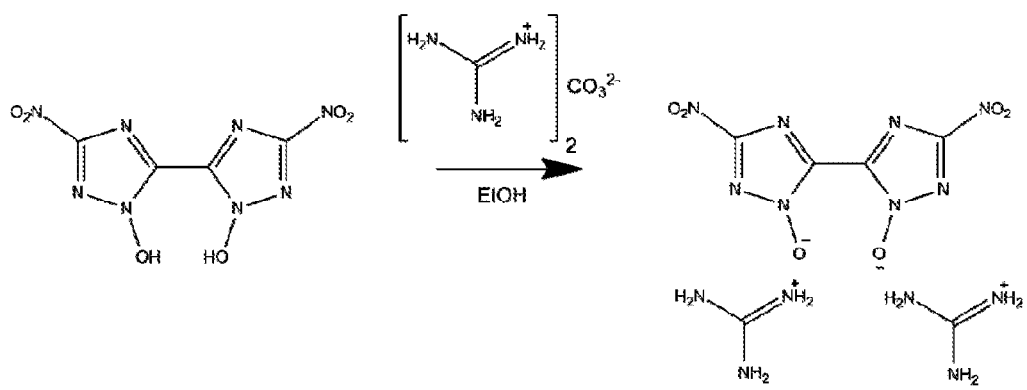
FIG. 5 is a diagrammatic representation of the synthesis of MAD-X2.

0.3 g (1.2 mmol) of DNBTO was dissolved in 50 mL of ethanol. To the solution there was added 0.22 g (1.2 mmol) of guanidinium carbonate. The mixture was heated to 60° C. for 30 min. The precipitate thus formed was separated as orange-colored solid by filtration. The separated solid was recrystallized from water. There was thus obtained 0.33 g (0.84 mmol) of MAD-X2. This corresponds to a yield of 71%. The reaction is illustrated diagrammatically in FIG. 5.

6. SYNTHESIS OF MAD-X3

Figure 6:
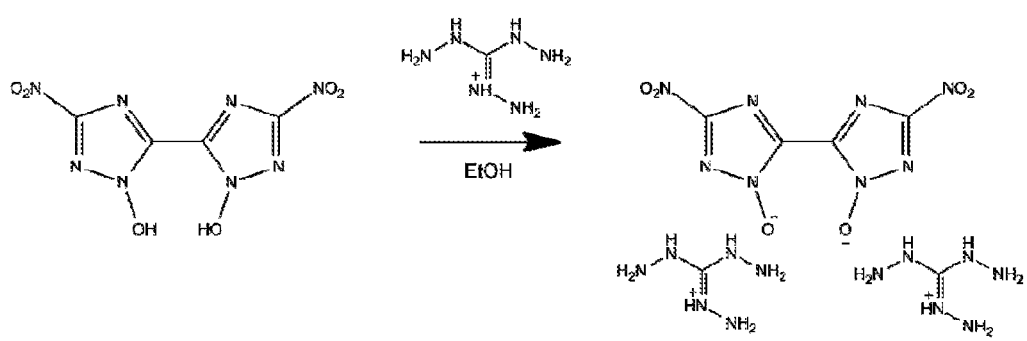
FIG. 6 is a diagrammatic representation of the synthesis of MAD-X3.

0.3 g (1.2 mmol) of DNBTO was dissolved in 50 mL of ethanol. To the solution there was added 0.25 g (2.4 mmol) of triaminoguanidine. The mixture was stirred at room temperature for 30 min. The precipitate thus formed was separated as orange-colored solid by filtration. The separated solid was recrystallized from water. There was thus obtained 0.47 g (1.0 mmol) of MAD-X3. This corresponds to a yield of 83%. The reaction is illustrated diagrammatically in FIG. 6.

With the syntheses of MAD-X1, MAD-X2, and MAD-X3 there is the advantage that DNBTO exhibits very good solubility in ethanol, whilst that of MAD-X2, MAD-X1, and MAD-X3 is very poor. As a result, the compounds can be isolated in good yields and with a high degree of purity.

The method according to the invention enables a synthesis from very inexpensive, easily available starting substances, solvents and reactants. The synthesis process involves only a small number of reaction steps and produces high yields. The method is thus very suitable for an industrial manufacturing process. Another great advantage lies in the fact that the reaction products obtained throughout the process are insensitive to external stimuli such as friction and impact. As a result, the method is very safe to handle.

We claim:

1. 3,3'-dinitro-5,5'-bis-triazole-1,1'-diol.

2. A salt of 3,3'-dinitro-5,5'-bis-triazole-1,1'-diol.

3. A salt as defined in claim 2, which is a dihydroxylammonium salt, a diguanidinium salt, or a di-triaminoguanidinium salt of 3,3'-dinitro-5,5'-bis-triazole-1,1'-diol.

4. An energetic active mass comprising a dihydroxylammonium salt, a diguanidinium salt, or a di-triaminoguanidinium salt of 3,3'-dinitro-5,5'-bis-triazole-1,1'-diol.

5. A method for the production of 3,3'-dinitro-5,5'-bis-triazole-1,1'-diol comprising the step of oxidizing 3,3'-dinitro-5,5'-bis-(1H-1,2,4-triazole) to provide 3,3'-dinitro-5,5'-bis-(triazole)-1,1'-diol.

6. A method as defined in claim 5, wherein said 3,3'-dinitro-5,5'-bis-(1H-1,2,4-triazole) is oxidized by an oxygen transfer agent selected from an inorganic or organic peroxoacid, perborate, hydrogen peroxide, or hypofluorous acid.

7. A method as defined in claim 5, wherein said 3,3'-dinitro-5,5'-bis-(1H-1,2,4-triazole) is obtained by diazotization of 3,3'-diamino-5,5'-bis-(1H-1,2,4-triazole) in sulfuric acid in the presence of nitrite.

8. A method as defined in claim 7, in which said 3,3'-diamino-5,5'-bis-(1H-1,2,4-triazole) is obtained by reaction of oxalic acid and aminoguanidine bicarbonate in an acid, separation of the intermediate thus formed, and heating said intermediate in a basic medium.

9. A method for the production of dihydroxylammonium salt, diguanidinium salt, or di-triaminoguanidinium salt of 3,3'-dinitro-5,5'-bis-triazole-1,1'-diol comprising the following steps:
   a) incubation of 3,3'-dinitro-5,5'-bis-(triazole)-1,1'-diol with hydroxylamine, hydroxylammonium ions, guanidinium carbonate, guanidinium ions, guanidine or tri-aminoguanidine in alcoholic solution, and
   b) separation of a precipitate thus formed.

10. An explosive, propellant, gas-producing pyrotechnic, or solid propellant additive comprising a dihydroxylammonium salt, a diguanidinium salt, or a di-triaminoguanidinium salt of 3,3'-dinitro-5,5'-bis-triazole-1,1'-diol.

11. A method as defined in claim 6, wherein said 3,3'-dinitro-5,5'-bis-(1H-1,2,4-triazole) is oxidized by $2KHSO_5 \cdot KHSO_4 \cdot K_2SO_4$.

12. A method as defined in claim 8, wherein the acid is concentrated hydrochloric acid.

\* \* \* \* \*